United States Patent  
Hidaka et al.

(10) Patent No.: US 7,012,159 B1
(45) Date of Patent: Mar. 14, 2006

(54) PHENOLIC COMPOUNDS AND RECORDING MATERIALS CONTAINING THE SAME

(75) Inventors: Tomoya Hidaka, Ichihara (JP); Shinichi Sato, Ichihara (JP); Tadashi Kawakami, Ichihara (JP)

(73) Assignee: Nippon Soda Co., Ltd., Tokyo (JP)

( * ) Notice: Subject to any disclaimer, the term of this patent is extended or adjusted under 35 U.S.C. 154(b) by 0 days.

(21) Appl. No.: 10/089,131

(22) PCT Filed: Oct. 4, 2000

(86) PCT No.: PCT/JP00/06892

§ 371 (c)(1),
(2), (4) Date: Mar. 25, 2002

(87) PCT Pub. No.: WO01/25193

PCT Pub. Date: Apr. 12, 2001

(30) Foreign Application Priority Data

Oct. 4, 1999 (JP) ............................................ 11-282577
Feb. 16, 2000 (JP) ........................................ 2000-037488

(51) Int. Cl.
  $C07C\ 233/05$ (2006.01)
  $C07C\ 321/12$ (2006.01)
  $C07C\ 317/02$ (2006.01)

(52) U.S. Cl. ................ 564/162; 106/31.28; 106/31.43; 430/552; 568/27; 568/28; 568/42; 568/43

(58) Field of Classification Search ................ 564/162; 568/27, 28, 42, 43; 106/31.28, 31.43; 430/552
See application file for complete search history.

(56) References Cited

U.S. PATENT DOCUMENTS 4,075,227 A   2/1978   Jones et al.
4,988,662 A   1/1991   Tsuchiya et al.
5,071,876 A  12/1991   Mueller et al.
5,614,357 A   3/1997   Lau et al.

FOREIGN PATENT DOCUMENTS

| EP | 0190682 A2 | 8/1988 |
|----|------------|--------|
| JP | 61-27955 A | 2/1986 |
| JP | 1-72891 A  | 3/1989 |
| JP | 64-72891   | 3/1989 |
| JP | 2-204091 A | 8/1990 |
| JP | 3-293195 A | 12/1991 |
| JP | 4-173775 A | 6/1992 |
| JP | 4-217657 A | 8/1992 |
| WO | WO 92/07825 | 5/1992 |
| WO | WO 00/28332 | 5/2000 |

*Primary Examiner*—Shailendra Kumar
(74) *Attorney, Agent, or Firm*—Dennis G. LaPointe

(57) ABSTRACT

Phenolic compounds of general formula (I);

$$(OH)_p\text{-Ar}(R^3)_q\text{-Y-}(CR^1R^2)_m\text{-S(O)}_n\text{-Ar}(R^4)_u(OH)_t \quad (I)$$

and recording materials characterized by containing one of them and exhibiting high light stability wherein $R^1$ and $R^2$ are each hydrogen or $C_1$–$C_6$ alkyl; m is an integer of 1 to 6; n is an integer of 0 to 2; p and t are each an integer of 0 to 3 with the proviso that not both are simultaneously 0; $R^3$ and $R^4$ are each nitro, carboxyl, halogeno, $C_1$–$C_6$ alkyl, or the like; q and u are each an integer of 0 to 2 with the proviso that when q or u is 2, $R^3$s or $R^4$s may be different from each other; and Y is CO or $NR^5$CO (wherein $R^5$ is hydrogen or the like), with the proviso that when Y is CO, p is 1 and that when p is 0 and Y is $NR^5$CO, n is not 0.

16 Claims, No Drawings

PHENOLIC COMPOUNDS AND RECORDING MATERIALS CONTAINING THE SAME

TECHNICAL FIELD OF INVENTION

The present invention is related to novel phenol compounds and recording materials containing the phenol compound and having excellent image storing and stabilizing properties.

BACKGROUND ART

Recording materials employing a manner of coloring by a reaction of a color forming dye and a developer have been widely used in thermal recording papers for recording outputted information from facsimiles, printers, etc. and pressure-sensitive copying papers for concurrently producing a plurality of copies, because such recording materials enable to record images in a short time by employing a relatively simple apparatus without requiring complex process such as development and fixation. As such recording materials, a material capable of instantly color forming, keeping whiteness of the part where no color is formed, hereinafter referred to as "background", and providing high hardness of the color formed images is required. However, in view of stability during storing in long-term basis, a recording material capable of providing excellent lightfastness to the color formed images is particularly desired. In this concern, development of color forming dyes, developers, stabilizers during storing, etc. has been tried in the field of this industry, however, a material having excellent sensitivity in color forming, giving whiteness on the background and image stability with a good balance and an enough satisfaction has not been obtained.

As compounds that are related to the present invention, in Jap. Pat. Appln. KOKAI Publication Nos. 2-204091, 1-72891 and 4-217657, the phenol compounds are disclosed as examples for a developer. In these disclosures, however, a technique to provide a recording material having high performance in the background effect and image stabilizing effects is sought. In addition, compounds similar to the compounds of the present invention are disclosed in Jap. Pat. Appln. KOKAI Publication Nos. 62-10502 and 61-27955, however, the use of these compounds is directed to an agricultural chemical, and all these compounds do not contain hydroxy group in the molecule that is essential for a developer.

DISCLOSURE OF THE INVENTION

The present invention is directed to phenol compounds represented by a general formula (I); wherein

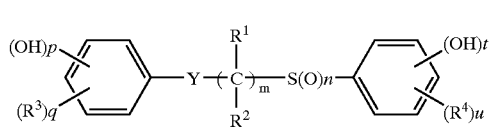

(I)

$R^1$ and $R^2$ represent hydrogen or C1–C6 alkyl, m represents an integer of 1 to 6, n represents an integer of 0 to 2, p and t represent an integer of 0 to 3, with proviso that p and t never be 0, concurrently, $R^3$ and $R^4$ represent nitro, carboxyl, halogen, C1–C6 alkyl, C1–C6 alkoxy, C1–C6 alkoxycarbonyl, sulfamoyl, phenylsulfamoyl, C1–C6 alkylsulfamoyl, di(C1–C6 alkyl)sulfamoyl, carbamoyl, phenylcarbamoyl, C1–C6 alkylcarbamoyl or di(C1–C6 alkyl)carbamoyl, q and u represent an integer of 0 to 2, $R^3$ and $R^4$ may be different to each other when q and u are 2, Y represents CO or $NR^5CO$, $R^5$ represents hydrogen, C1–C6 alkyl, optionally-substituted phenyl or optionally-substituted benzyl, with proviso that p is 1 when Y is CO, and n is not 0 when p is 0 and Y is $NR^5CO$, and a recording material characterized by comprising at least one of said phenol compounds.

In the general formula (I), examples for the group represented by $R^1$ and $R^2$ include hydrogen; C1–C6 alkyl, such as methyl, ethyl, n-propyl, isopropyl, n-butyl, sec-butyl, tert-butyl, n-pentyl, isopentyl, neopentyl, tert-pentyl, n-hexyl, isohexyl, 1-methylpentyl and 2-methylpentyl, examples for the group represented by $R^3$ and $R^4$ include nitro, carboxyl, sulfamoyl, carbamoyl, phenylsulfamoyl, phenylcarbamoyl; halogen, such as fluorine, chlorine, bromine and iodine; C1–C6 alkyl, such as methyl, ethyl, n-propyl, isopropyl, n-butyl, sec-butyl, tert-butyl, n-pentyl, isopentyl, neopentyl, tert-pentyl, n-hexyl, isohexyl, 1-methylpentyl and 2-methylpentyl; C1–C6 alkoxy, such as methoxy, ethoxy, n-propoxy, isopropoxy, n-butoxy, sec-butoxy and tert-butoxy; C1–C6 alkoxycarbonyl, such as methoxycarbonyl, ethoxycarbonyl, propoxycarbonyl and isopropoxycarbonyl; C1–C6 alkylsulfamoyl, such as methylsulfamoyl, ethylsulfamoyl and propylsulfamoyl; di(C1–C6 alkyl)sulfamoyl, such as dimethylsulfamoyl, diethylsulfamoyl and methylethylsulfamoyl; C1–C6 alkylsulcarbamoyl, such as methylcarbamoyl, ethylcarbamoyl and propylcarbamoyl; and di(C1–C6 alkyl)carbamoyl, such as dimethylcarbamoyl, diethylcarbamoyl and methylethylcarbamoyl, and examples for the group represented $R^5$ include hydrogen; C1–C6 alkyl, such as methyl, ethyl, n-propyl, isopropyl, n-butyl, sec-butyl, tert-butyl, n-pentyl, isopentyl, neopentyl, tert-pentyl, n-hexyl, isohexyl, 1-methylpentyl and 2-methylpenty; optionally-substituted phenyl; and optionally-substituted benzyl;

wherein examples for said substituent include hydrogen, hydroxy; halogen, such as fluorine, chlorine, bromine and iodine; C1–C6 alkyl, such as methyl, ethyl, n-propyl, isopropyl, n-butyl, sec-butyl, tert-butyl, n-pentyl, isopentyl, neopentyl, tert-pentyl, n-hexyl, isohexyl, 1-methylpentyl and 2-methylpenty; and C1–C6 alkoxy, such as methoxy, ethoxy, n-propoxy, isopropoxy, n-butoxy, sec-butoxy and tert-butoxy.

The compounds represented by the general formula (I), wherein the portion of S(O)n is S, to be used in the present invention may be obtained by forcing a compound represented by a general formula (VI);

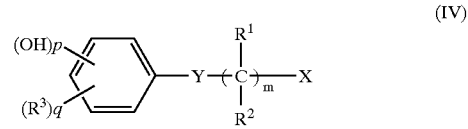

(IV)

Wherein $R^1$, $R^2$, $R^3$, Y, m, p and q are as defined above, X represents halogen, such as chlorine and bromine, to a reaction with a compound represented by a general formula (V);

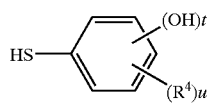

(V)

wherein $R^4$, t and u are as defined above, in an organic solvent, for example, methanol in the presence of a base.

Compounds represented by the general formula (I), wherein the portion of $S(O)n$ is SO or $SO_2$, may be obtained by oxidizing the compound obtained by the reaction hereinabove with an oxidizing agent, such as aqueous solution of hydrogen peroxide and m-chloroperbenzoic acid in an appropriate solvent.

The compounds those, which may be synthesized according to the process, described above are presented in Tables 1 and 2.

TABLE 1

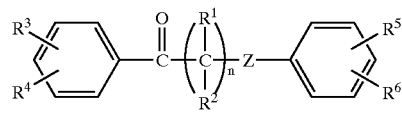

| Compound No. | $R^3$ | $R^4$ | $R^1$ | $R^2$ | n | Z | $R^5$ | $R^6$ | Melting Point (° C.) |
|---|---|---|---|---|---|---|---|---|---|
| I-1 | 2-OH | H | H | H | 1 | S | H | H | |
| I-2 | 2-OH | H | H | H | 1 | SO | H | H | |
| I-3 | 2-OH | H | H | H | 1 | $SO_2$ | H | H | |
| I-4 | 2-OH | H | H | H | 1 | S | 4-OH | H | 139–141 |
| I-5 | 2-OH | H | H | H | 1 | SO | 4-OH | H | 166–167 |
| I-6 | 2-OH | H | H | H | 1 | $SO_2$ | 4-OH | H | 143–146 |
| I-7 | 2-OH | H | H | H | 2 | S | 4-OH | H | |
| I-8 | 2-OH | H | H | H | 2 | SO | 4-OH | H | |
| I-9 | 2-OH | H | H | H | 2 | $SO_2$ | 4-OH | H | |
| I-10 | 2-OH | H | H | H | 3 | S | 4-OH | H | |
| I-11 | 2-OH | H | H | H | 3 | SO | 4-OH | H | |
| I-12 | 2-OH | H | H | H | 3 | $SO_2$ | 4-OH | H | |
| I-13 | 2-OH | H | H | H | 4 | S | 4-OH | H | |
| I-14 | 2-OH | H | H | H | 4 | SO | 4-OH | H | |
| I-15 | 2-OH | H | H | H | 4 | $SO_2$ | 4-OH | H | |
| I-16 | 2-OH | 5-$CH_3$ | H | H | 1 | S | 4-OH | H | |
| I-17 | 2-OH | 5-$CH_3$ | H | H | 1 | SO | 4-OH | H | |
| I-18 | 2-OH | 5-$CH_3$ | H | H | 1 | $SO_2$ | 4-OH | H | |
| I-19 | 2-OH | 5-Cl | H | H | 1 | S | 4-OH | H | |
| I-20 | 2-OH | 5-Cl | H | H | 1 | SO | 4-OH | H | |
| I-21 | 2-OH | 5-Cl | H | H | 1 | $SO_2$ | 4-OH | H | |
| I-22 | 2-OH | 5-Br | H | H | 1 | S | 4-OH | H | |
| I-23 | 2-OH | 5-Br | H | H | 1 | SO | 4-OH | H | |
| I-24 | 2-OH | 5-Br | H | H | 1 | $SO_2$ | 4-OH | H | |
| I-25 | 2-OH | 4-$OCH_3$ | H | H | 1 | S | 4-OH | H | |
| I-26 | 2-OH | 4-$OCH_3$ | H | H | 1 | SO | 4-OH | H | |
| I-27 | 2-OH | 4-$OCH_3$ | H | H | 1 | $SO_2$ | 4-OH | H | |
| I-28 | 2-OH | 5-$OCH_3$ | H | H | 1 | S | 4-OH | H | |
| I-29 | 2-OH | 5-$OCH_3$ | H | H | 1 | SO | 4-OH | H | |
| I-30 | 2-OH | 5-$OCH_3$ | H | H | 1 | $SO_2$ | 4-OH | H | |
| I-31 | 2-OH | H | $CH_3$ | H | 1 | S | 4-OH | H | |
| I-32 | 2-OH | H | $CH_3$ | H | 1 | SO | 4-OH | H | |
| I-33 | 2-OH | H | $CH_3$ | H | 1 | $SO_2$ | 4-OH | H | |
| I-34 | 2-OH | H | $CH_3$ | $CH_3$ | 1 | S | 4-OH | H | |
| I-35 | 2-OH | H | $CH_3$ | $CH_3$ | 1 | SO | 4-OH | H | |
| I-36 | 2-OH | H | $CH_3$ | $CH_3$ | 1 | $SO_2$ | 4-OH | H | |
| I-37 | 2-OH | H | H | H | 1 | S | 2-OH | 4-OH | |
| I-38 | 2-OH | H | H | H | 1 | SO | 2-OH | 4-OH | |
| I-39 | 2-OH | H | H | H | 1 | $SO_2$ | 2-OH | 4-OH | |
| I-40 | 2-OH | H | H | H | 1 | S | 2-OH | 5-OH | |
| I-41 | 2-OH | H | H | H | 1 | SO | 2-OH | 5-OH | |
| I-42 | 2-OH | H | H | H | 1 | $SO_2$ | 2-OH | 5-OH | |
| I-43 | 2-OH | H | H | H | 1 | S | 2-OH | 5-$CH_3$ | |
| I-44 | 2-OH | H | H | H | 1 | SO | 2-OH | 5-$CH_3$ | |
| I-45 | 2-OH | H | H | H | 1 | $SO_2$ | 2-OH | 5-$CH_3$ | |
| I-46 | 2-OH | H | H | H | 1 | S | 3-$CH_3$ | 4-OH | |
| I-47 | 2-OH | H | H | H | 1 | SO | 3-$CH_3$ | 4-OH | |
| I-48 | 2-OH | H | H | H | 1 | $SO_2$ | 3-$CH_3$ | 4-OH | |
| I-49 | 2-OH | H | H | H | 1 | S | 3-Cl | 4-OH | |
| I-50 | 2-OH | H | H | H | 1 | SO | 3-Cl | 4-OH | |
| I-51 | 2-OH | H | H | H | 1 | $SO_2$ | 3-Cl | 4-OH | |
| I-52 | 2-OH | H | H | H | 1 | S | 2-$CH_3$ | 4-OH | |
| I-53 | 2-OH | H | H | H | 1 | SO | 2-$CH_3$ | 4-OH | |
| I-54 | 2-OH | H | H | H | 1 | $SO_2$ | 2-$CH_3$ | 4-OH | |
| I-55 | 3-OH | H | H | H | 1 | S | H | H | |
| I-56 | 3-OH | H | H | H | 1 | SO | H | H | |

TABLE 1-continued

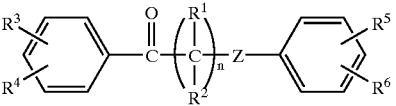

| Compound No. | R³ | R⁴ | R¹ | R² | n | Z | R⁵ | R⁶ | Melting Point (° C.) |
|---|---|---|---|---|---|---|---|---|---|
| I-57 | 3-OH | H | H | H | 1 | SO₂ | H | H | |
| I-58 | 3-OH | H | H | H | 1 | S | 4-OH | H | 156–159 |
| I-59 | 3-OH | H | H | H | 1 | SO | 4-OH | H | 155–157 |
| I-60 | 3-OH | H | H | H | 1 | SO₂ | 4-OH | H | 189–192 |
| I-61 | 3-OH | H | H | H | 2 | S | 4-OH | H | |
| I-62 | 3-OH | H | H | H | 2 | SO | 4-OH | H | |
| I-63 | 3-OH | H | H | H | 2 | SO₂ | 4-OH | H | |
| I-64 | 3-OH | H | H | H | 3 | S | 4-OH | H | |
| I-65 | 3-OH | H | H | H | 3 | SO | 4-OH | H | |
| I-66 | 3-OH | H | H | H | 3 | SO₂ | 4-OH | H | |
| I-67 | 3-OH | H | H | H | 4 | S | 4-OH | H | |
| I-68 | 3-OH | H | H | H | 4 | SO | 4-OH | H | |
| I-69 | 3-OH | H | H | H | 4 | SO₂ | 4-OH | H | |
| I-70 | 3-OH | 5-CH₃ | H | H | 1 | S | 4-OH | H | |
| I-71 | 3-OH | 5-CH₃ | H | H | 1 | SO | 4-OH | H | |
| I-72 | 3-OH | 5-CH₃ | H | H | 1 | SO₂ | 4-OH | H | |
| I-73 | 3-OH | 5-Cl | H | H | 1 | S | 4-OH | H | |
| I-74 | 3-OH | 5-Cl | H | H | 1 | SO | 4-OH | H | |
| I-75 | 3-OH | 5-Cl | H | H | 1 | SO₂ | 4-OH | H | |
| I-76 | 3-OH | 4-OCH₃ | H | H | 1 | S | 4-OH | H | |
| I-77 | 3-OH | 4-OCH₃ | H | H | 1 | SO | 4-OH | H | |
| I-78 | 3-OH | 4-OCH₃ | H | H | 1 | SO₂ | 4-OH | H | |
| I-79 | 3-OH | H | CH₃ | H | 1 | S | 4-OH | H | |
| I-80 | 3-OH | H | CH₃ | H | 1 | SO | 4-OH | H | |
| I-81 | 3-OH | H | CH₃ | H | 1 | SO₂ | 4-OH | H | |
| I-82 | 3-OH | H | CH₃ | CH₃ | 1 | S | 4-OH | H | |
| I-83 | 3-OH | H | CH₃ | CH₃ | 1 | SO | 4-OH | H | |
| I-84 | 3-OH | H | CH₃ | CH₃ | 1 | SO₂ | 4-OH | H | |
| I-85 | 3-OH | H | H | H | 1 | S | 2-OH | 4-OH | |
| I-86 | 3-OH | H | H | H | 1 | SO | 2-OH | 4-OH | |
| I-87 | 3-OH | H | H | H | 1 | SO₂ | 2-OH | 4-OH | |
| I-88 | 3-OH | H | H | H | 1 | S | 2-OH | 5-OH | |
| I-89 | 3-OH | H | H | H | 1 | SO | 2-OH | 5-OH | |
| I-90 | 3-OH | H | H | H | 1 | SO₂ | 2-OH | 5-OH | |
| I-91 | 3-OH | H | H | H | 1 | S | 2-OH | 5-CH3 | |
| I-92 | 3-OH | H | H | H | 1 | SO | 2-OH | 5-CH3 | |
| I-93 | 3-OH | H | H | H | 1 | SO₂ | 2-OH | 5-CH3 | |
| I-94 | 3-OH | H | H | H | 1 | S | 3-CH₃ | 4-OH | |
| I-95 | 3-OH | H | H | H | 1 | SO | 3-CH₃ | 4-OH | |
| I-96 | 3-OH | H | H | H | 1 | SO₂ | 3-CH₃ | 4-OH | |
| I-97 | 3-OH | H | H | H | 1 | S | 3-Cl | 4-OH | |
| I-98 | 3-OH | H | H | H | 1 | SO | 3-Cl | 4-OH | |
| I-99 | 3-OH | H | H | H | 1 | SO₂ | 3-Cl | 4-OH | |
| I-100 | 3-OH | H | H | H | 1 | S | 2-CH₃ | 4-OH | |
| I-101 | 3-OH | H | H | H | 1 | SO | 2-CH₃ | 4-OH | |
| I-102 | 3-OH | H | H | H | 1 | SO₂ | 2-CH₃ | 4-OH | |
| I-103 | 4-OH | H | H | H | 1 | S | H | H | 168–171 |
| I-104 | 4-OH | H | H | H | 1 | SO | H | H | |
| I-105 | 4-OH | H | H | H | 1 | SO₂ | H | H | 154–156 |
| I-106 | 4-OH | H | H | H | 1 | S | 4-OH | H | 194–197 |
| I-107 | 4-OH | H | H | H | 1 | SO | 4-OH | H | 167–169 |
| I-108 | 4-OH | H | H | H | 1 | SO₂ | 4-OH | H | 212–214 |
| I-109 | 4-OH | H | H | H | 2 | S | 4-OH | H | |
| I-110 | 4-OH | H | H | H | 2 | SO | 4-OH | H | |
| I-111 | 4-OH | H | H | H | 2 | SO₂ | 4-OH | H | |
| I-112 | 4-OH | H | H | H | 3 | S | 4-OH | H | |
| I-113 | 4-OH | H | H | H | 3 | SO | 4-OH | H | |
| I-114 | 4-OH | H | H | H | 3 | SO₂ | 4-OH | H | |
| I-115 | 4-OH | H | H | H | 4 | S | 4-OH | H | |
| I-116 | 4-OH | H | H | H | 4 | SO | 4-OH | H | |
| I-117 | 4-OH | H | H | H | 4 | SO₂ | 4-OH | H | |
| I-118 | 2-CH₃ | 4-OH | H | H | 1 | S | 4-OH | H | 94–96 |
| I-119 | 2-CH₃ | 4-OH | H | H | 1 | SO | 4-OH | H | |
| I-120 | 2-CH₃ | 4-OH | H | H | 1 | SO₂ | 4-OH | H | 187–189 |
| I-121 | 3-CH₃ | 4-OH | H | H | 1 | S | 4-OH | H | |
| I-122 | 3-CH₃ | 4-OH | H | H | 1 | SO | 4-OH | H | |
| I-123 | 3-CH₃ | 4-OH | H | H | 1 | SO₂ | 4-OH | H | |
| I-124 | 3-Cl | 4-OH | H | H | 1 | S | 4-OH | H | |

TABLE 1-continued

[Structure: R³,R⁴-substituted phenyl-C(=O)-(CR¹R²)ₙ-Z-phenyl-R⁵,R⁶]

| Compound No. | R³ | R⁴ | R¹ | R² | n | Z | R⁵ | R⁶ | Melting Point (° C.) |
|---|---|---|---|---|---|---|---|---|---|
| I-125 | 3-Cl | 4-OH | H | H | 1 | SO | 4-OH | H | |
| I-126 | 3-Cl | 4-OH | H | H | 1 | SO₂ | 4-OH | H | |
| I-127 | 3-Br | 4-OH | H | H | 1 | S | 4-OH | H | |
| I-128 | 3-Br | 4-OH | H | H | 1 | SO | 4-OH | H | |
| I-129 | 3-Br | 4-OH | H | H | 1 | SO₂ | 4-OH | H | |
| I-130 | 3-CH₃ | 4-OH | H | H | 1 | S | 4-OH | H | |
| I-131 | 3-CH₃ | 4-OH | H | H | 1 | SO | 4-OH | H | |
| I-132 | 3-CH₃ | 4-OH | H | H | 1 | SO₂ | 4-OH | H | |
| I-133 | 4-OH | H | CH₃ | H | 1 | S | 4-OH | H | |
| I-134 | 4-OH | H | CH₃ | H | 1 | SO | 4-OH | H | |
| I-135 | 4-OH | H | CH₃ | H | 1 | SO₂ | 4-OH | H | |
| I-136 | 4-OH | H | CH₃ | CH₃ | 1 | S | 4-OH | H | |
| I-137 | 4-OH | H | CH₃ | CH₃ | 1 | SO | 4-OH | H | |
| I-138 | 4-OH | H | CH₃ | CH₃ | 1 | SO₂ | 4-OH | H | |
| I-139 | 4-OH | H | H | H | 1 | S | 2-OH | 4-OH | 178–180 |
| I-140 | 4-OH | H | H | H | 1 | SO | 2-OH | 4-OH | |
| I-141 | 4-OH | H | H | H | 1 | SO₂ | 2-OH | 4-OH | 224–226 |
| I-142 | 4-OH | H | H | H | 1 | S | 2-OH | 5-OH | |
| I-143 | 4-OH | H | H | H | 1 | SO | 2-OH | 5-OH | |
| I-144 | 4-OH | H | H | H | 1 | SO₂ | 2-OH | 5-OH | |
| I-145 | 4-OH | H | H | H | 1 | S | 2-OH | 5-CH₃ | 145–147 |
| I-146 | 4-OH | H | H | H | 1 | SO | 2-OH | 5-CH₃ | |
| I-147 | 4-OH | H | H | H | 1 | SO₂ | 2-OH | 5-CH₃ | 180–183 |
| I-148 | 4-OH | H | H | H | 1 | S | 3-CH₃ | 4-OH | |
| I-149 | 4-OH | H | H | H | 1 | SO | 3-CH₃ | 4-OH | |
| I-150 | 4-OH | H | H | H | 1 | SO₂ | 3-CH₃ | 4-OH | |
| I-151 | 4-OH | H | H | H | 1 | S | 3-Cl | 4-OH | |
| I-152 | 4-OH | H | H | H | 1 | SO | 3-Cl | 4-OH | |
| I-153 | 4-OH | H | H | H | 1 | SO₂ | 3-Cl | 4-OH | |
| I-154 | 4-OH | H | H | H | 1 | S | 2-CH₃ | 4-OH | 150–152 |
| I-155 | 4-OH | H | H | H | 1 | SO | 2-CH₃ | 4-OH | |
| I-156 | 4-OH | H | H | H | 1 | SO₂ | 2-CH₃ | 4-OH | 207–209 |
| I-157 | 4-NO₂ | H | H | H | 1 | SO₂ | 4-OH | H | 184–186 |
| I-158 | 4-OH | 2-OH | H | H | 1 | S | 4-OH | H | 122–125 |

TABLE 2

[Structure: R³,R⁴-substituted phenyl-N(R⁷)-C(=O)-(CR¹R²)ₙ-Z-phenyl-R⁵,R⁶]

| Compound No. | R³ | R⁴ | R⁷ | R¹ | R² | n | Z | R⁵ | R⁶ | Melting Point |
|---|---|---|---|---|---|---|---|---|---|---|
| II-1 | H | H | H | H | H | 1 | SO | 4-OH | H | 208–210 |
| II-2 | H | H | H | H | H | 1 | SO₂ | 4-OH | H | 188–189 |
| II-3 | H | H | H | H | H | 2 | SO | 4-OH | H | |
| II-4 | H | H | H | H | H | 2 | SO₂ | 4-OH | H | 191–193 |
| II-5 | H | H | H | H | H | 1 | SO | 2-OH | 4-OH | |
| II-6 | H | H | H | H | H | 1 | SO₂ | 2-OH | 4-OH | 222–224 |
| II-7 | H | H | H | H | H | 1 | SO | 2-OH | 5-OH | |
| II-8 | H | H | H | H | H | 1 | SO₂ | 2-OH | 5-OH | |
| II-9 | H | H | H | H | H | 1 | SO | 2-CH₃ | 4-OH | |
| II-10 | H | H | H | H | H | 1 | SO₂ | 2-CH₃ | 4-OH | |
| II-11 | H | H | H | H | H | 1 | SO | 2-CH₃ | 4-OH | |
| II-12 | H | H | H | H | H | 1 | SO₂ | 2-CH₃ | 4-OH | |
| II-13 | H | H | H | H | H | 1 | SO | 2-CH₃ | 5-OH | |
| II-14 | H | H | H | H | H | 1 | SO₂ | 2-CH₃ | 5-OH | |
| II-15 | H | H | H | CH₃ | H | 1 | SO | 4-OH | H | 138–139 |
| II-16 | H | H | H | CH₃ | H | 1 | SO₂ | 4-OH | H | 194–196 |
| II-17 | 2-CH₃ | H | H | H | H | 1 | SO | 4-OH | H | |
| II-18 | 2-CH₃ | H | H | H | H | 1 | SO₂ | 4-OH | H | |
| II-19 | 3-CH₃ | H | H | H | H | 1 | SO | 4-OH | H | |
| II-20 | 3-CH₃ | H | H | H | H | 1 | SO₂ | 4-OH | H | |

TABLE 2-continued

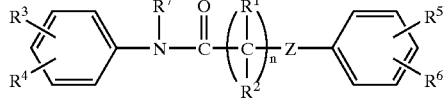

| Compound No. | R³ | R⁴ | R⁷ | R¹ | R² | n | Z | R⁵ | R⁶ | Melting Point |
|---|---|---|---|---|---|---|---|---|---|---|
| II-21 | 4-CH₃ | H | H | H | H | 1 | SO | 4-OH | H | |
| II-22 | 4-CH₃ | H | H | H | H | 1 | SO₂ | 4-OH | H | 203–204 |
| II-23 | 4-Cl | H | H | H | H | 1 | SO | 4-OH | H | |
| II-24 | 4-Cl | H | H | H | H | 1 | SO₂ | 4-OH | H | 212–213 |
| II-25 | 4-Br | H | H | H | H | 1 | SO | 4-OH | H | |
| II-26 | 4-Br | H | H | H | H | 1 | SO₂ | 4-OH | H | |
| II-27 | 2-OCH₃ | H | H | H | H | 1 | SO | 4-OH | H | |
| II-28 | 2-OCH₃ | H | H | H | H | 1 | SO₂ | 4-OH | H | 158–161 |
| II-29 | 3-OCH₃ | H | H | H | H | 1 | SO | 4-OH | H | |
| II-30 | 3-OCH₃ | H | H | H | H | 1 | SO₂ | 4-OH | H | 178–180 |
| II-31 | 4-OCH₃ | H | H | H | H | 1 | SO | 4-OH | H | |
| II-32 | 4-OCH₃ | H | H | H | H | 1 | SO₂ | 4-OH | H | 185–188 |
| II-33 | 2-CO₂CH₃ | H | H | H | H | 1 | SO | 4-OH | H | |
| II-34 | 2-CO₂CH₃ | H | H | H | H | 1 | SO₂ | 4-OH | H | |
| II-35 | 3-CO₂CH₃ | H | H | H | H | 1 | SO | 4-OH | H | |
| II-36 | 3-CO₂CH₃ | H | H | H | H | 1 | SO₂ | 4-OH | H | |
| II-37 | 4-CO₂CH₃ | H | H | H | H | 1 | SO | 4-OH | H | |
| II-38 | 4-CO₂CH₃ | H | H | H | H | 1 | SO₂ | 4-OH | H | 232–235 |
| II-39 | 3-CO₂CH₂CH₃ | H | H | H | H | 1 | SO | 4-OH | H | |
| II-40 | 3-CO₂CH₂CH₃ | H | H | H | H | 1 | SO₂ | 4-OH | H | |
| II-41 | 4-CO₂CH₂CH₃ | H | H | H | H | 1 | SO | 4-OH | H | |
| II-42 | 4-CO₂CH₂CH₃ | H | H | H | H | 1 | SO₂ | 4-OH | H | 203–205 |
| II-43 | 2-CO₂H | H | H | H | H | 1 | SO | 4-OH | H | |
| II-44 | 2-CO₂H | H | H | H | H | 1 | SO₂ | 4-OH | H | |
| II-45 | 3-CO₂H | H | H | H | H | 1 | SO | 4-OH | H | |
| II-46 | 3-CO₂H | H | H | H | H | 1 | SO₂ | 4-OH | H | |
| II-47 | 4-CO₂H | H | H | H | H | 1 | SO | 4-OH | H | |
| II-48 | 4-CO₂H | H | H | H | H | 1 | SO₂ | 4-OH | H | 285–286 |
| II-49 | 3-CONHCH₃ | H | H | H | H | 1 | SO | 4-OH | H | |
| II-50 | 3-CONHCH₃ | H | H | H | H | 1 | SO₂ | 4-OH | H | |
| II-51 | 4-CONHPh | H | H | H | H | 1 | SO | 4-OH | H | |
| II-52 | 4-CONHPh | H | H | H | H | 1 | SO₂ | 4-OH | H | |
| II-53 | 3-CON(CH₃)₂ | H | H | H | H | 1 | SO | 4-OH | H | |
| II-54 | 3-CON(CH₃)₂ | H | H | H | H | 1 | SO₂ | 4-OH | H | |
| II-55 | 2-SO₂NH₂ | H | H | H | H | 1 | SO | 4-OH | H | |
| II-56 | 2-SO₂NH₂ | H | H | H | H | 1 | SO₂ | 4-OH | H | |
| II-57 | 3-SO₂NH₂ | H | H | H | H | 1 | SO | 4-OH | H | |
| II-58 | 3-SO₂NH₂ | H | H | H | H | 1 | SO₂ | 4-OH | H | |
| II-59 | 4-SO₂NH₂ | H | H | H | H | 1 | SO | 4-OH | H | |
| II-60 | 4-SO₂NH₂ | H | H | H | H | 1 | SO₂ | 4-OH | H | 285–287 |
| II-61 | 4-SO₂NHPh | H | H | H | H | 1 | SO | 4-OH | H | |
| II-62 | 4-SO₂NHPh | H | H | H | H | 1 | SO₂ | 4-OH | H | |
| II-63 | H | H | Ph | H | H | 1 | SO | 4-OH | H | |
| II-64 | H | H | Ph | H | H | 1 | SO₂ | 4-OH | H | 265–269 |
| II-65 | 2-OH | H | H | H | H | 1 | S | 4-OH | H | 176–179 |
| II-66 | 2-OH | H | H | H | H | 1 | SO | 4-OH | H | |
| II-67 | 2-OH | H | H | H | H | 1 | SO₂ | 4-OH | H | 190–192 |
| II-68 | 2-OH | 4-CH₃ | H | H | H | 1 | S | 4-OH | H | |
| II-69 | 2-OH | 4-CH₃ | H | H | H | 1 | SO | 4-OH | H | |
| II-70 | 2-OH | 4-CH₃ | H | H | H | 1 | SO₂ | 4-OH | H | |
| II-71 | 2-OH | 4-OCH₃ | H | H | H | 1 | S | 4-OH | H | |
| II-72 | 2-OH | 4-OCH₃ | H | H | H | 1 | SO | 4-OH | H | |
| II-73 | 2-OH | 4-OCH₃ | H | H | H | 1 | SO₂ | 4-OH | H | |
| II-74 | 2-OH | H | H | H | H | 1 | S | H | H | 141–142 |
| II-75 | 2-OH | H | H | H | H | 1 | SO | H | H | |
| II-76 | 2-OH | H | H | H | H | 1 | SO₂ | H | H | |
| II-77 | 2-OH | H | CH₃ | H | H | 1 | S | 4-OH | H | |
| II-78 | 2-OH | H | CH₃ | H | H | 1 | SO | 4-OH | H | |
| II-79 | 2-OH | H | CH₃ | H | H | 1 | SO₂ | 4-OH | H | |
| II-80 | 2-OH | H | Ph | H | H | 1 | S | 4-OH | H | |
| II-81 | 2-OH | H | Ph | H | H | 1 | SO | 4-OH | H | |
| II-82 | 2-OH | H | Ph | H | H | 1 | SO₂ | 4-OH | H | |
| II-83 | 3-OH | H | H | H | H | 1 | S | 4-OH | H | 171–173 |
| II-84 | 3-OH | H | H | H | H | 1 | SO | 4-OH | H | 202–204 |
| II-85 | 3-OH | H | H | H | H | 1 | SO₂ | 4-OH | H | 254–256 |
| II-86 | 3-OH | 4-CH₃ | H | H | H | 1 | S | 4-OH | H | 181–182 |
| II-87 | 3-OH | 4-CH₃ | H | H | H | 1 | SO | 4-OH | H | |
| II-88 | 3-OH | 4-CH₃ | H | H | H | 1 | SO₂ | 4-OH | H | 200–203 |
| II-89 | 3-OH | H | H | H | H | 1 | S | H | H | |

TABLE 2-continued $$R^3\underset{R^4}{\diagdown}\text{Ph}-\underset{R^7}{N}-\underset{O}{\overset{O}{C}}-(\underset{R^2}{\overset{R^1}{C}})_n-Z-\text{Ph}\underset{R^6}{\diagup}R^5$$

| Compound No. | R³ | R⁴ | R⁷ | R¹ | R² | n | Z | R⁵ | R⁶ | Melting Point |
|---|---|---|---|---|---|---|---|---|---|---|
| II-90 | 3-OH | H | H | H | H | 1 | SO | H | H | |
| II-91 | 3-OH | H | H | H | H | 1 | SO₂ | H | H | |
| II-92 | 3-OH | H | CH₃ | H | H | 1 | S | 4-OH | H | |
| II-93 | 3-OH | H | CH₃ | H | H | 1 | SO | 4-OH | H | |
| II-94 | 3-OH | H | CH₃ | H | H | 1 | SO₂ | 4-OH | H | |
| II-95 | 3-OH | H | Ph | H | H | 1 | S | 4-OH | H | 158–159 |
| II-96 | 3-OH | H | Ph | H | H | 1 | SO | 4-OH | H | 191–192 |
| II-97 | 3-OH | H | Ph | H | H | 1 | SO₂ | 4-OH | H | 238–239 |
| II-98 | 4-OH | H | H | H | H | 1 | S | 4-OH | H | 163–164 |
| II-99 | 4-OH | H | H | H | H | 1 | SO | 4-OH | H | 220–221 |
| II-100 | 4-OH | H | H | H | H | 1 | SO₂ | 4-OH | H | 211–215 |
| II-101 | 4-OH | H | H | H | H | 1 | S | H | H | |
| II-102 | 4-OH | H | H | H | H | 1 | SO | H | H | |
| II-103 | 4-OH | H | H | H | H | 1 | SO₂ | H | H | |
| II-104 | 4-OH | H | CH₃ | H | H | 1 | S | 4-OH | H | |
| II-105 | 4-OH | H | CH₃ | H | H | 1 | SO | 4-OH | H | |
| II-106 | 4-OH | H | CH₃ | H | H | 1 | SO₂ | 4-OH | H | |
| II-107 | 4-OH | H | Ph | H | H | 1 | S | 4-OH | H | 180–181 |
| II-108 | 4-OH | H | Ph | H | H | 1 | SO | 4-OH | H | 215–217 |
| II-109 | 4-OH | H | Ph | H | H | 1 | SO₂ | 4-OH | H | 276–277 |
| II-110 | 3-OH | H | (3-OH)Ph | H | H | 1 | S | 4-OH | H | |
| II-111 | 3-OH | H | (3-OH)Ph | H | H | 1 | SO | 4-OH | H | |
| II-112 | 3-OH | H | (3-OH)Ph | H | H | 1 | SO₂ | 4-OH | H | |
| II-113 | 4-OH | H | (4-OH)Ph | H | H | 1 | S | 4-OH | H | |
| II-114 | 4-OH | H | (4-OH)Ph | H | H | 1 | SO | 4-OH | H | |
| II-115 | 4-OH | H | (4-OH)Ph | H | H | 1 | SO₂ | 4-OH | H | |
| II-116 | 2-CH₃ | 4-OCH₃ | H | H | H | 1 | SO₂ | 4-OH | H | 164–167 |
| II-117 | 4-SO₂NH₂ | 2-OH | H | H | H | 1 | S | 4-OH | H | 221–225 |
| II-118 | 3-OCH₃ | H | Ph | H | H | 1 | SO₂ | 4-OH | H | 205–208 |
| II-119 | 4-OCH₃ | 2-CH₃ | Ph | H | H | 1 | SO₂ | 4-OH | H | 228–230 |
| II-120 | 3-OH | H | c-Hexyl | H | H | 1 | S | 4-OH | H | 193–196 |
| II-121 | 3-OH | H | c-Hexyl | H | H | 1 | SO₂ | 4-OH | H | 240–243 |
| II-122 | 2-OH | H | H | H | H | 2 | S | 4-OH | H | 134–139 |
| II-123 | 2-OH | H | H | H | H | 2 | SO₂ | 4-OH | H | 156–157 |
| II-124 | 2-NO₂ | 4-OCH₃ | H | H | H | 2 | SO₂ | 4-OH | H | 130–132 |
| II-125 | 2-OH | H | H | CH₃ | H | 1 | S | 4-OH | H | 166–171 |
| II-126 | 2-OH | 4-NO₂ | H | H | H | 1 | S | 4-OH | H | 232–233 |
| II-127 | 2-OH | 5-Cl | H | H | H | 1 | S | 4-OH | H | 185–186 |
| II-128 | 2-OH | 5-CH₃ | H | H | H | 1 | S | 4-OH | H | 174–176 |

The present invention may be applied for any use for recording materials as far as they employ a color forming dye, for example, for thermal recording materials and pressure-sensitive copying materials.

When the present invention is used for thermal recording papers, it can be applied according to the same method for applying a known stabilizer for image keeping and developer. For example, each of a compound of the present invention in fine particles and a color forming dye in fine particles are dispersed in an aqueous solution of an aqueous binding agent, such as polyvinyl alcohol and cellulose, and the resultant suspension is mixed and coated onto a support material, for example a paper, and then dried to obtain a thermal recording paper.

The ratio of the compound represented by the general formula (I) of the present invention to be used with respect to a color forming dye is 1 to 10 parts by weight based on 1 part by weight of a color forming dye, and preferably 1.5 to 5 parts by weight.

The recording material of the present invention may also contain one or more of a known developer, an image stabilizer, a sensitizer, a filler, a dispersing agent, an antioxidant, a desensitizer, an antitack agent, an antifoamer, a photo stabilizer, a fluorescence brightener, and the like upon requirement in addition to a color forming dye and the compound represented by the general formula (I).

These additional agents may be contained either in the color former layer, or in an arbitrary layer, for example a protecting layer when the recording material is configured by a multi-layer structure. In particular, when an overcoat layer and an undercoat layer are provided to the upper and under portions of a color former layer, an antioxidant, a photosensitizer and the like may be contained in these layers. Further, said antioxidant and photosensitizer may be contained in the overcoat and undercoat layers in a form of microcapsules in which these agents are enclosed.

Examples of the color forming dye used for the recording material of the present invention include leuco dyes based on fluoran, phthalide, lactam, triphenyl methane, fenothiazine, and spiropyran. However, the color forming dyes are not limited to these leuco dyes, and any color forming dyes may be used as far as it forms color by contacting with a developer of an acidic substance. Each of these color forming dyes can form a color independently, and it naturally constitutes a recording material having a color that is formed by the color forming dye, and two or more of these color forming dyes may be used in combination. For example, a recording material that forms true black may be prepared by combining color forming dyes each forming red, blue and green and a color forming dye forming black.

Examples of the color forming dyes based on fluoran include 3-diethylamino-6-methyl-7-anilinofluoran, 3-dibutylamino-6-methyl-7-anilinofluoran, 3-(N-ethyl-N-isobutylamino)-6-methyl-7-anilinofluoran, 3-(N-methyl-N-propylamino)-6-methyl-7-anilinofluoran, 3-(N-ethyl-N-isopentylamino)-6-methyl-7-anilinofluoran, 3-diethylamino-7-(o-chloroanilino)fluoran, 3-dibutylamino-7-(o-chloroanilino)fluoran, 3-(N-ethyl-p-toluidino)-6-methyl-7-anilinofluoran, 3-(N-cyclohexyl-N-methylamino)-6-methyl-7-anilinofluoran, 3-pyrrolidino-6-methyl-7-aralinofluoran, 3-piperidino-6-methyl-7-aralinofluoran, 3-dimethylamino-7-(m-trifluoromethylanilino)fluoran, 3-dipentylamino-6-methyl-7-anilinofluoran, 3-(N-ethoxypropyl-N-ethylamino)-6-methyl-7-anilinofluoran, 3-dibutylamino-7-(o-fluoroanilino)fluoran, 3-diethylaminobenzo[a]fluoran, 3-dimethylamino-6-methyl-7-chlorofluoran, 3-diethylamino-5-methyl-7-dibenzylaminofluoran, 3-diethylamino-7-dibenzylaminofluoran, 3-diethylamino-5-chlorofluoran, 3-diethylamino-6-(N,N'-dibenzylamino)fluoran, 3,6-domethoxyfluoran, and 2,4-dimethyl-6-(4-dimethylaminophenyl)aminofluoran.

As a near infrared absorbing dye, 3-(4-(4-(4-anilino)-anilino)anilino-6-methyl-7-chlorofluoran, 3,3-bis(2-(4-dimethylaminophenyl)-2-(4-methoxyphenyl)vinyl)-4,5,6,7-tetrachlorophthalide, 3,6,6'-tris(dimethylamino)spiro [fluorine-9,3'-phthalide and the like may be exampled.

Other than the above, 3,3-bis(4'-diethylaminophenyl)-6-diethylaminophthalide and the like are also exampled.

Examples for the developer include bisphenol compounds, such as bisphenol A, 4,4'-sec-butylidenebisphenol, 4,4'-cyclohexylidenebisphenol, 2,2-dimethyl-3,3-bis(4-hydroxyphenyl)butane, 2,2'-dihydroxydiphenyl, pentamethylene-bis(4-hydroxybenzoate), 2,2-dimethyl-3,3-di(4-hydroxyphenyl)pentane, 2,2-di(4-hydroxyphenyl)hexane; metal salts of benzoic acid, such as zinc benzoate and zinc 4-nitrobenzoate; salicylates, such as salicylic 4-(2-(4-methoxyphenyloxy)ethyloxy); metal salts of salicylic acid, such as zinc salicylate and bis[4-(octyloxycarbonylamino)-2-hydroxybenzoic acid; hydroxysulfones, such as 4,4'-dihydroxydiphenylsulfone, 2,4'-dihydroxydiphenylsulfone, 4-hydroxy-4'-methyldiphenylsulfone, 4-hydroxy-4'-isopropoxydiphenylsulfone, 4-hydroxy-4'-benzyloxydiphenylsulfone, 4-hydroxy-4'-butoxydiphenylsulfone, 4,4'-dihydroxy-3,31-diallyldiphenylsulfone, 3,4-dihydroxy-4'-methyldiphenylsulfone, 4,4'-dihydroxy-3,3',5,5'-tetrabromodiphenylsulfone; 4-hydroxyphthalic diesters, such as dimethyl 4-hydroxyphthalate, dicyclohexyl 4-hydroxyphthalate and diphenyl 4-hydroxyphthalate; hydroxynaphthoic esters, such as 2-hydroxy-6-carboxynaphthalene; hydroxyacetophenone, p-phenylphenol, benzyl 4-hydroxyphenylacetate, p-benzylphenol, hydroquonine-monobenzyl ether; trihalomethylsulfones, such as tribromomethylphenylsulfone; sulfonylureas such as 4,4'-bis(p-toluenesulfonylaminocarbonylamino)diphenylmethane; tetracyanoqinodimethanes; 2,4-dihydroxy-2'-methoxybenzanilide and diphenylsulfone bridged compounds represented by a formula (VI);

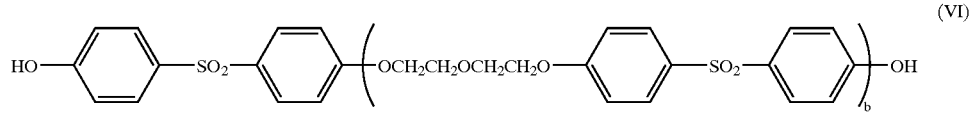

(VI)

wherein b is an integer of 0 to 6, and mixtures of the compounds described above.

Examples for the image stabilizing agent include epoxy-containing diphenylsulfones, such as 4-benzyloxy-4'-(2-methylglycidyloxy)-diphenylsulfone, and 4,4'-diglycidyloxydiphenylsulfone; 1,4-diglycidyloxybenzene; 4-(α-(hydroxymethyl)benzyloxy)-4'-hydroxydiphenylsulfone; 2-propanol derivatives; salicylic acid derivatives; metal salts of oxynaphthoic acid derivatives (particularly, zinc salts) and other water-insoluble zinc-containing compounds.

Examples for the sensitizer include higher fatty acid amides, such as stearic amide, benzamide, stearic anilide, acetoacetic anilide, thioacetoanilide, dibenzyl oxalate, di(4-methylbenzyl) oxalate, di(4-chlorobenzyl) oxalate, dimethyl phthalate, dimethyl telephthalate, dibenzyl telephthalate, dibenzyl isophthalate, bis(tert-butylphenol)s, diethers of 4,4'-dihydroxydiphenylsulfone, diethers of 2,4'-dihydroxydiphenylsulfone, 1,2-bis(phenoxy)ethane, 1,2-bis(4-methylphenoxy)ethane, 1,2-bis(3-methylphenoxy)ethane, 2-naphtholbenzyl ether, diphenylamine, carbazole, 2,3-di-m-tolylbutane, 4-benzylbiphenyl, 4,4'-dimethylbiphenyl, m-terphenyl, di-β-naphthylphenylene diamine, phenyl 1-hydroxy-naphthoate, 2-naphthylbenzyl ether, 4-methylphenyl-biphenyl ether, 2,2-bis(3,4-dimethylphenyl)ethane, and 2,3,5,6-tetramethyl-4'-methyldiphenylmethane.

As the filler, silica, clay, kaolin, burned kaolin, talc, satin white, aluminum hydroxide, calcium carbonate, magnesium carbonate, zinc oxide, titanium oxide, barium sulfate, magnesium silicate, aluminum silicate, plastic pigment and the like may be used. In the recording material of the present invention, salts of alkaline earth metals are particularly preferable, and carbonates, such as calcium carbonate and magnesium carbonate are further preferable. The ratio of the filler to be used is 0.1 to 15 parts by weight, preferably 1 to 10 parts by weight, relative to 1 part by weight of a color forming dye. In addition, other types of fillers may be used in combination with the above-mentioned materials.

Examples for the dispersing agent include sulfosuccinic esters, such as dioctylsodium sulfosuccinate, sodium dodecylbenzene sulfonate, and sodium salt and fatty acid salt of lauryl alcohol sulfuric ester.

Examples for the antioxidant include 2,2'-methylenebis(4-methyl-6-tert-butylphenol), 2,2'-methylenebis(4-ethyl-6-tert-butylphenol), 4,4'-propylmethylenebis(3-methyl-6-tert-butylphenol), 4,4'-bytylidenebis(3-methyl-6-tert-butylphenol), 4,4'-thiobis(2-tert-butyl-5-methylphenol), 1,1,3-tris(2-methyl-4-hydroxy-5-tert-butylphenyl)butane, and 1,1,3-tris(2-methyl-4-hydroxy-5-cyclohexylphenyl)butane. Among these examples, 2,2'-methylenebis(4-methyl-6-tert-butylphenol), 2,2'-methylenebis(4-ethyl-6-tert-butylphenol), 4,4'-propylmethylenebis(3-methyl-6-tert-butylphenol), 1,1,3-tris(2-methyl-4-hydroxy-5-tert-butylphenyl)butane, and 1,1,3-tris(2-methyl-4-hydroxy-5-cyclohexylphenyl)butane are particularly effective compounds for improving a heat and humidity of the compounds according to the present invention. In particular, 1,1,3-tris(2-methyl-4-hydroxy-5-tert-butylphenyl)butane, and 1,1,3-tris(2-methyl-4-hydroxy-5-cyclohexylphenyl) butane have excellent effect against heat and humidity.

As the desensitizer, aliphatic higher alcohols, polyethylene glycol, guanidine derivatives and the like may be exampled.

Examples for the antitack agent include stearic acid, zinc stearate, calcium stearate, carnauba wax, paraffin wax, and ester wax.

Examples for the photostabilizing agent include salicylic acid based ultraviolet radiation absorbents, such as phenyl salicylate, p-tert-butylphenyl salicylate and p-octylphenyl salicylate; benzophenone based ultraviolet radiation absorbents, such as 2,4-dihydroxybenzophenone, 2-hydroxy-4-methoxybenzophenone, 2-hydroxy-4-benzyloxybenzophenone, 2-hydroxy-4-octyloxybenzophenone, 2-hydroxy-4-dodecyloxybenzophenone, 2,2'-dihydroxy-4-methoxybenzophenone, 2,2'-dihydroxy-4,4'-dimethoxybenzophenone and 2-hydroxy-4-methoxy-5-sulfobenzophenone; benzotriazole based ultraviolet radiation absorbents, such as 2-(2'-hydroxy-5'-methylphenyl)benzotriazole, 2-(2'-hydroxy-5'-tert-butylphenyl)benzotriazole, 2-(2'-hydroxy-3',5'-di-tert-butylphenyl)benzotriazole, 2-(2'-hydroxy-3'-tert-butyl-5'-methylphenyl)-5-chlorobenzotriazole, 2-(2'-hydroxy-3',5'-di-tert-butylphenyl)-5-chlorobenzotriazole, 2-(2'-hydroxy-3',5'-di-tert-amylphenyl)benzotriazole, 2-[2'-hydroxy-3'-(3",4",5",6"-tetrahydrophthalimidemethyl)-5'-tert-methylphenyl]benzotriazole, 2-(2'-hydroxy-5'-tert-octylphenyl)benzotriazole, 2-[2'-hydroxy-3',5'-bis(α,α-dimethylbenzyl)phenyl]-2H-benzotriazole, 2-(2'-hydroxy-3'-dodecyl-5'-methylphenyl)benzotriazole, 2-(2'-hydroxy-3'-undecyl-5'-methylphenyl)benzotriazole, 2-(2'-hydroxy-3'-undecyl-5'-methylphenyl)benzotriazole, 2-(2'-hydroxy-3'-tridodecyl-5'-methylphenyl)benzotriazole, 2-(2'-hydroxy-3'-tetradecyl-5'-methylphenyl)benzotriazole, 2-(2'-hydroxy-3'-pentadecyl-5'-methylphenyl)benzotriazole, 2-(2'-hydroxy-3'-hexadecyl-5'-methylphenyl)henzotriazole, 2-[2'-hydroxy-4'-(2'-ethylhexyl)oxyphenyl]benzotriazole, 2-[2'-hydroxy-4'-(2"-ethylheptyl)oxyphenyl]benzotriazole, 2-[2'-hydroxy-4'-(2"-ethyloctyl)oxyphenyl]benzotriazole, 2-[2'-hydroxy-4'-(2"-propyloctyl)oxyphenyl]benzotriazole, 2-[2-hydroxy-4'-(2"-propylheptyl)oxyphenyl]benzotriazole, 2-[2'-hydroxy-4'-(2"-propylhexyl)oxyphenyl]benzotriazole, 2-[2'-hydroxy-4'-(1"-ethylhexyl)oxyphenyl]benzotriazole, 2-[2'-hydroxy-4'- (1"-ethylheptyl)oxyphenyl]benzotriazole, 2-[2'-hydroxy-4'-(1'-ethyloctyl)oxyphenyl]benzotriazole, 2-[2'-hydroxy-4'-(1"-propyloctyl)oxyphenyl]benzotriazole, 2-[2'-hydroxy-4'-(1"-propylheptyl)oxyphenyl] benzotriazole, 2-[2'-hydroxy-4'-(1"-propylhexyl)oxyphenyl] benzotriazole, and a condensate of polyethylene glycol and methyl-3-[3-tert-butyl-5-(2H-benzotriazole-2-yl)-4-hydroxyphenyl]propionate; cyanoacrylate based ultraviolet radiation absorbents, such as 2'-ethylhexyl-2-cyano-3,3-diphenylacrylate and ethyl-2-cyano-3,3-diphenylacrylate; and hindered amine based ultraviolet radiation absorbents, such as bis(2,2,6,6-tetramethyl-4-piperidyl)sebacate, succinic acid-bis(2,2,6,6-tetramethyl-4-piperidyl) ester and 2-(3,5-di-tert-butyl)malonate-bis(1,2,2,6,6-pentamethyl-4-piperidyl) ester.

Examples for the fluorescent dye include 4,4'-bis[2-anilino-4-(2-hydroxyethyl)amino-1,3,5-triazinyl-6-aminolstilbene-2,2'-disulfonic acid disodium salt, 4,4'-bis[2-anilino-4-bis(hydroxyethyl)amino-1,3,5-triazinyl-6-amino] stilbene-2,2'-disulfonic acid disodium salt, 4,4'-bis[2-methoxy-4-(2-hydroxyethyl)amino-1,3,5-triazinyl-6-amino] stilbene-2,2'-disulfonic acid disodium salt, 4,4'-bis[2-methoxy-4-(2-hydroxypropyl)amino-1,3,5-triazinyl-6-amino]stilbene-2,2'-disulfonic acid disodium salt, 4,4'-bis[2-m-sulfoanilino-4-bis(hydroxyethyl)amino-1,3,5-triazinyl-6-amino]stilbene-2,2'-disulfonic acid disodium salt, 4-[2-p-sulfoanilino-4-bis(hydroxyethyl)amino-1,3,5-triazinyl-6-amino]-4'-[2-m-sulfoanilino-4-bis(hydroxyethyl)amino-1,3,5-triazinyl-6-amino]stilbene-2,2'-disulfonic acid tetrasodium salt, 4,4'-bis[2-p-sulfoanilino-4-bis(hydroxyethyl)amino-1,3,5-triazinyl-6-amino]stilbene-2,2'-disulfonic acid tetrasodium salt, 4,4'-bis[2-(2,5-disulfoanilino)-4-phenoxyamino-1,3,5-triazinyl-6-amino] stilbene-2,2'-disulfonic acid hexasodium salt, 4,4'-bis[2-(2,5-disulfoanilino)-4-(p-methoxycarbonylphenoxy)amino-1,3,5-triazinyl-6-amino]stilbene-2,2'-disulfonic acid hexasodium salt, 4,4'-bis[2-(p-sulfophenoxy)-4-bis(hydroxyethyl)amino-1,3,5-triazinyl-6-amino]stilbene-2,2'-disulfonic acid tetrasodium salt, 4,4'-bis[2-(2,5-disulfoanilino)-4-formalinylamino-1,3,5-triazinyl-6-amino] stilbene-2,2'-disulfonic acid hexasodium salt and 4,4'-bis[2-(2,5-disulfoanilino)-4-bis(hydroxyethyl)amino-1,3,5-triazinyl-6-amino]stilbene-2,2'-disulfonic acid hexasodium salt.

The compounds of the present invention may be used for producing pressure-sensitive copying papers according to the same process for using a known image storing and stabilizing agent, a known developer and a known sensitizer. For example, a color forming dye prepared into a form of microcapsule is dispersed by using an appropriated dispersing agent according to a known procedure, and the resultant dispersion is coated onto a paper to obtain a sheet coated with a color forming dye. On the other hand, a dispersion of a developer is coated onto a paper to prepare a sheet coated with a developer. At that time, when the compound of the present invention is used as an image storing and stabilizing agent, the compound may be used by means of incorporating it into a dispersed solution of any component to be used for preparing a coupler sheet or a developer sheet. The both sheets prepared as described above are combined to prepare a pressure-sensitive copying paper. The pressure-sensitive copying paper may be an unit paper comprising an upper layer sheet holding a microcapsule layer enclosing an organic solvent solution of a color forming dye onto the underside face and an under sheet layer holding a developer (an acidic substance) onto the upper side face or self content paper coated with the microcapsule dispersion and a developer dispersion on the identical face of a support paper.

As the developer to be used for producing pressure-sensitive copying papers and the developer to be used in combination with the compound of the present invention for the same application, known developers having been conventionally used may be used. Examples for such developers include inorganic acidic substance, such as acid clay, activated clay, apataljite, bentonite, colloidal silica, aluminum silicate, magnesium silicate, zinc silicate, tin silicate, burned kaolin and talc; aliphatic carboxylic acid, such as oxalic acid, maleic acid, tartaric acid, citric acid, succinic acid and suiaric acid; aromatic carboxylic acid, such as benzoic acid, p-tert-butylbenzoic acid, phthalic acid, gallic acid, salicylic acid, 3-isopropylsalicylic acid, 3-phenylsalicylic acid, 3-cyclohexylsalicylic acid, 3,5-di-tert-butylsalicylic acid, 3-methyl-5-benzylsalicylic acid, 3-phenyl-5-(2,2-dimethylbenzyl)salicylic acid, 3,5-di-(2-methylbenzyl) salicylic acid, and 2-hydroxy-1-benzyl-3-naphthoic acid; metal salts, such as zinc, magnesium, aluminum and titanium salts, of the above-mentioned aliphatic carboxylic acids; phenol resin based developers, such as p-phenylphenol-formalin resin and p-butylphenol-acetylene resin; and mixtures of said phenol resin based developer and a metal salt of said aromatic carboxylic acid.

BEST MODES FOR CARRYING OUT THE INVENTION

Now, the compounds of the present invention is further described in detail with referring the examples in the following. Note that the part indicated below in the examples denotes a part by weight.

EXAMPLE 1

Synthesis of 2'-hydroxy-2-(4-hydroxyphenylthio) acetophenone (Compound No. I-4)

10.0 g (79.4 mmol) of 4-mercaptophenol, 5.3 g (80.4 mmol) of potassium hydroxide and 100 mL of methanol were added under a room temperature into a 200 mL flask with four inlets and attached with a stirrer and a thermometer. After confirming that potassium hydroxide added is completely dissolved, temperature inside the resultant solution was cooled down to 10° C., then 16.9 g (78.6 mmol) of 2'-hydroxyphenacyl bromide was added to the solution and stirred for 3 hours at a room temperature. Following to the completion of the reaction, the solution was extracted with methyl isobutyl ketone, hereinafter referred to as MIBK, and MIBK was distilled out of the extract under reduced pressure. The obtained residue was subjected to recrystallization process with toluene to thereby obtain 19.0 g of 2'-hydroxy-2-(4-hydroxyphenylthio)acetophenone. The yield was 93% and the melting point thereof was in a range of 139 to 141° C.

EXAMPLE 2

Synthesis of 2'-hydroxy-2-(4-hydroxyphenylsulfinyl) acetophenone (Compound No. I-5)

6.0 g (23.1 mmol) of 2'-hydroxy-2-(4-hydroxyphenylthio) acetophenone and 50 mL of acetic acid were added under a room temperature into a 100 mL flask with four inlets and attached with a stirrer and a thermometer. To the resultant solution, 2.8 g (24.7 mmol) of 30% aqueous solution of hydrogen peroxide was added, and the solution was stirred for 12 hours at a room temperature. Following to the completion of the reaction, 0.5 g of dimethyl sulfide was added into the solution, and then, the solution was extracted with MIBK. The MIBK layer was washed several times with water, and followed by washing with sodium hydrogencarbonate. The MIBK in the solution was distilled out under reduced pressure, and the resultant residue was subjected to recrystallization with ethyl acetate to obtain 4.5 g of 2'-hydroxy-2-(4-hydroxyphenylsulfinyl) acetophenone. The yield was 71% and the melting point of the compound was in a range of 166 to 167° C.

EXAMPLE 3

Synthesis of 2'-hydroxy-2-(4-hydroxyphenylsulfonyl) acetophenone (Compound No. I-6)

6.0 g (23.1 mmol) of 2'-hydroxy-2-(4-hydroxyphenylthio) acetophenone and 50 mL of chloroform were added under a room temperature into a 100 mL flask with four inlets and attached with a stirrer and a thermometer. To the resultant solution, 11.2 g (48.5 mmol) of m-perchlorobenzoic acid (purity 75%) was added a few at a time under a room temperature, and the solution was stirred for 4 hours. Following to the completion of the reaction, 0.5 g of dimethyl sulfide was added into the solution, and then, the solution was extracted with chloroform. The chloroform layer was washed with aqueous solution of sodium hydrogencarbonate. The chloroform in the solution was distilled out under reduced pressure, and the resultant residue was subjected to recrystallization with toluene to obtain 5.0 g of 2'-hydroxy-2-(4-hydroxyphenylsulfonyl)acetophenone. The yield was 74% and the melting point of the compound was in a range of 143 to 146° C.

EXAMPLE 4

Synthesis of 4'-hydroxy-2-(4-hydroxyphenylthio) acetophenone (Compound No. I-106)

4'-hydroxy-2-(4-hydroxyphenylthio)acetophenone in an amount of 17.5 g was obtained by proceeding the same reaction and post-reaction as described in the Example 1, except that 2'-hydroxyphenacyl bromide is replaced by 4'-hydroxyphenacyl bromide. The yield was 86% and the melting point of the compound was in a range of 194 to 197° C.

EXAMPLE 5

Synthesis of 4'-hydroxy-2-(4-hydroxyphenylsulfinyl) acetophenone (Compound No. I-107)

4'-hydroxy-2-(4-hydroxyphenylsulfinyl)acetophenone in an amount of 4.8 g was obtained according to the same process as described in the Example 2, except that 2'-hydroxy-2-(4-hydroxyphenylthio)acetophenone is replaced by 4'-hydroxy-2-(4-hydroxyphenylthio) acetophenone. The yield was 75% and the melting point of the compound was in a range of 167 to 169° C.

EXAMPLE 6

Synthesis of 4'-hydroxy-2-(4-hydroxyphenylsulfonyl) acetophenone (Compound No. I-108)

4'-hydroxy-2-(4-hydroxyphenylsulfonyl)acetophenone in an amount of 5.4 g was obtained according to the same process as described in the Example 3, except that 2'-hydroxy-2-(4-hydroxyphenylthio)acetophenone is replaced by 4'-hydroxy-2-(4-hydroxyphenylthio) acetophenone. The yield was 80% and the melting point of the compound was in a range of 212 to 214° C.

EXAMPLE 7

Synthesis of 2-(4-hydroxyphenylsulfinyl)acetoanilide (Compound No. II-1)

6.0 g (23.2 mmol) of 2-(4-hydroxyphenylthio) acetoanilide and 50 mL of acetic acid were added under a room temperature into a 100 mL flask with four inlets and attached with a stirrer and a thermometer. To the resultant solution, 2.8 g (24.7 mmol) of 30k aqueous solution of hydrogen peroxide was added, and the resultant solution was stirred for 12 hours at a room temperature. Following to the completion of the reaction, 0.5 g of dimethyl sulfide was added into the solution, and then, the solution was extracted with MIBK. The MIBK layer was washed several times with water, and followed by washing with sodium hydrogencarbonate. The MIBK in the solution was distilled out under reduced pressure, and the resultant residue was subjected to recrystallization with MIBK to obtain 5.9 g of 2-(4-hydroxyphenylsulfinyl)acetoanilide. The yield was 93% and the melting point of the compound was in a range of 208 to 210° C.

EXAMPLE 8

Synthesis of 2-(4-hydroxyphenylsulfonyl)acetoanilide (Compound No. II-2)

6.0 g (23.2 mmol) of 2-(4-hydroxyphenylthio) acetoanilide and 50 mL of acetic acid were added under a room temperature into a 100 mL flask with four inlets and attached with a stirrer and a thermometer. To the resultant solution, 5.6 g (49.4 mmol) of 30% aqueous solution of hydrogen peroxide was added, and the solution was stirred for 4 hours at a room temperature and consequently for 5 hours at 100° C. Following to the completion of the reaction, 0.5 g of dimethyl sulfide was added into the solution, and then, the solution was extracted with MIBK. The MIBK layer was washed several times with water, and followed by washing with sodium hydrogencarbonate. The MIBK in the solution was distilled out under reduced pressure, and the resultant residue was subjected to recrystallization with MIBK to obtain 5.8 g of 2-(4-hydroxphenylsulfonyl) acetoanilide. The yield was 86% and the melting point of the compound was in a range of 188 to 189° C.

EXAMPLE 9

Preparation of Thermal Recording Papers

| Dye dispersion (A solution) | |
| --- | --- |
| 3-di-n-butylamino-6-methyl-7-anilinofluoran | 16 parts |
| 10% aqueous solution of polyvinyl alcohol | 84 parts |
| Developer dispersion (B solution) | |
| 4'-hydroxy-2-(4-hydroxyphenylsulfonyl)acetophenone (Compound No. I-108) | 16 parts |
| 10% aqueous solution of polyvinyl alcohol | 84 parts |
| Filler dispersion (C solution) | |
| Calcium carbonate | 27.8 parts |
| 10% aqueous solution of polyvinyl alcohol | 26.2 parts |
| Water | 71 parts |

All components for each of A solution, B solution and C solution shown above were mixed and thoroughly grinded by using a sand grinder, respectively, to prepare each dispersed solutions of A to C. 1 part by weight of A solution, 2 parts by weight of B solution and 4 parts by weight of C solution were mixed to prepare a coating solution. The coating solution was coated onto a white paper by using a wire rod (No. 12) and then dried. The coated paper was then subjected to calendaring to prepare a thermal recording paper. (The amount of the coating solution based on the dry weight was approximately 5.5 g/m$^2$.)

EXAMPLE 10

The thermal recording material of the present invention was prepared according to the same process as described in Example 9, except that 3'-hydroxy-2-(4-hydroxyphenylsulfonyl)acetophenone (Compound No. I-60) was used in place of the developer used in Example 9.

EXAMPLE 11

The thermal recording material of the present invention was prepared according to the same process as described in Example 9, except that 2-(4-hydroxyphenylsulfonyl) acetoanilide (Compound No. II-2) was used in place of the developer used in Example 9.

EXAMPLE 12

The thermal recording material of the present invention was prepared according to the same process as described in Example 9, except that 2'-hydroxy-(4-hydroxyphenylthio)-2-acetoanilide (Compound No. II-65) was used in place of the developer used in Example 9.

EXAMPLE 13

The thermal recording material of the present invention was prepared according to the same process as described in Example 9, except that 2-(4-hydroxyphenylthio)-(2'-hydroxy-5'-chloro)acetoanilide (Compound No. II-127) was used in place of the developer used in Example 9.

EXAMPLE 14

The thermal recording material of the present invention was prepared according to the same process as described in Example 9, except that 2-phenylthio-2'-hydroxy-acetoanilide (Compound No. II-74) was used in place of the developer used in Example 9.

COMPARATIVE EXAMPLE 1

The thermal recording material of the present invention was prepared according to the same process as described in Example 9, except that 4-hydroxy-4'-isopropoxydiphenylsulfone was used in place of the developer used in Example 9.

COMPARATIVE EXAMPLE 2

The thermal recording material of the present invention was prepared according to the same process as described in Example 9, except that 2,4'-dihydroxydiphenylsulfone was used in place of the developer used in Example 9.

COMPARATIVE EXAMPLE 3

Compound Disclosed in Jap. Pat. No. 2615073

The thermal recording material of the present invention was prepared according to the same process as described in Example 9, except that 2-(4-hydroxyphenylsulfonyl) acetophenone was used in place of the developer used in Example 9.

COMPARATIVE EXAMPLE 4

Compound Disclosed in Jap. Pat. Appln. KOKAI Publication No. 2-204091

The thermal recording material of the present invention was prepared according to the same process as described in Example 9, except that 3',4'-dihydroxy-2-(4-hydroxyphenylsulfonyl)acetophenone was used in place of the developer used in Example 9.

COMPARATIVE EXAMPLE 5

Compound Disclosed in Jap. Pat. Appln. KOKAI Publication No. 4-217657

The thermal recording material of the present invention was prepared according to the same process as described in Example 9, except that 2-(4-hydroxyphenylthio)acetoanilide was used in place of the developer used in Example 9.

TEST EXAMPLE 1

Comparison in Dynamic Sensitivity

The thermal recording papers prepared in Examples 9 to 12 and Comparative Examples 1 to 4 were recorded under a condition of 0.38 mJ and 0.50 mJ per dot by using Thermal Recording Paper Color Forming Testing Apparatus (manufactured by Okura Denki Co., Ltd., Type: TH-PMD), and the density of the images was measured by means of Macbeth densitometer, RD-514. The results are shown in Table 3.

TABLE 3

Evaluation Results of Dynamic Sensitivity

| | Quantity of Energy | |
|---|---|---|
| | 0.38 mj/dot | 0.50 mj/dot |
| Example 9 | 0.36 | 0.82 |
| Example 10 | 0.42 | 0.90 |
| Example 11 | 0.36 | 0.90 |
| Example 12 | 0.33 | 0.94 |
| Comparative Example 1 | 0.85 | 1.19 |
| Comparative Example 2 | 0.57 | 1.15 |
| Comparative Example 3 | 0.88 | 1.19 |
| Comparative Example 4 | 0.21 | 0.47 |

*FIGS. indicated in the table denote Macbeth values.

TEST EXAMPLE 2

Heat and Humidity Test

Each of the thermal recording papers prepared in Examples 9 to 14 and Comparative Examples 1 to 5 were recorded according to the same procedures as described in Test Example 1. A heat and humidity test was conducted for the images being recorded to the saturated state in a thermohygrostat, Type: GL-42, manufactured by Futaba Science, under a temperature of 50° C. and humidity of 80%. The density of the color formed images after 2 and 24 hours were measured. The results are shown in Table 4.

TEST EXAMPLE 3 lightfast Test

Each of the thermal recording papers prepared in Examples 9 to 14 and Comparative Examples 1 to 5 was recorded according to the same procedures as described in Test Example 1. The images were subjected to lightfast tests where a lightfast testing apparatus (Ultraviolet Radiation Long Life Fade Meter, Type: FAL-5, manufactured by Suga Shikenki Co., Ltd.) is employed for the measurement. The densities of the tested images after 48 hours were-measured. The results are shown in Table 4.

TABLE 4

(Evaluation Results on Backgrounds and Images)

| | Background | | | Image | | | | |
|---|---|---|---|---|---|---|---|---|
| | Orig- | Heat and Humidity | | Orig- | Lightfastness | | | |
| | inal | 2 hr | 24 hr | inal | 6 hr | 12 hr | 24 hr | 48 hr |
| Example 9 | 0.05 | 0.05 | 0.05 | 1.13 | 1.10 <98> | 1.06 <94> | 1.03 <91> | 0.95 <85> |
| Example 10 | 0.06 | 0.07 | 0.07 | 1.12 | 1.14 <102> | 1.09 <97> | 1.06 <94> | 0.90 <80> |
| Example 11 | 0.05 | 0.05 | 0.05 | 1.17 | 1.11 <95> | 0.98 <83> | 0.91 <78> | 0.74 <63> |
| Example 12 | 0.07 | 0.06 | 0.06 | 1.32 | 1.29 <98> | 1.26 <95> | 1.33 <101> | 1.35 <102> |
| Example 13 | 0.06 | 0.06 | 0.06 | 1.23 | 1.20 <98> | 1.21 <98> | 1.13 <92> | 1.07 <87> |
| Example 14 | 0.05 | 0.05 | 0.05 | 0.58 | 0.65 <112> | 0.57 <98> | 0.55 <95> | 0.48 <83> |
| Comparative Example 1 | 0.08 | 0.07 | 0.07 | 1.26 | 1.08 <86> | 0.60 <48> | 0.29 <23> | 0.14 <11> |
| Comparative Example 2 | 0.10 | 0.10 | 0.10 | 1.25 | 1.19 <96> | 1.08 <87> | 0.96 <76> | 0.76 <61> |
| Comparative Example 3 | 0.11 | 0.16 | 0.18 | 1.22 | 1.23 <101> | 1.11 <91> | 1.00 <82> | 0.59 <48> |
| Comparative Example 4 | 0.09 | 0.09 | 0.09 | 1.06 | 1.03 <97> | 0.96 <91> | 0.82 <77> | 0.72 <68> |
| Comparative Example 5 | 0.04 | 0.04 | 0.05 | 1.25 | 1.23 <98> | 1.14 <91> | 1.07 <85> | 0.89 <72> |

* Figures indicated in the table denote Macbeth values, and the figures in < > denote residual image ratio.

Advantageous Effect of the Invention

The recording material using the phenol compound of the present invention as a developer provides images with more improved storing and stabilizing property than images formed with conventional recording materials. With the phenol compounds of the present invention, a recording material having excellent dynamic sensitivity and preservative properties of image and background can be obtained.

What is claimed is:

1. Phenol compounds represented by a general formula (I);

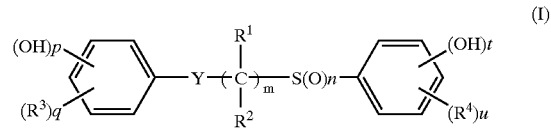

wherein $R^1$ and $R^2$ represent hydrogen or C1–C6 alkyl, m represents an integer of 1 to 6, n represents an integer of 0 to 2, p and t represent an integer of 0 to 3, with proviso that p and t never be $0_3$ concurrently, $R^3$ and $R^4$ represent nitro, carboxyl, halogen, C1–C6 alkyl, C1–C6 alkoxy, C1–C6 alkoxycarbonyl, sulfamoyl, phenylsulfamoyl, C1–C6 alkylsulfamoyl, di(C1–C6 alkylsulfamoyl), carbamoyl, phenylcarbamoyl, C1–C6 alkylcarbamoyl or di(C1–C6 alkylcarbamoyl), q and u represent an integer of 0 to 2, $R^3$ and $R^4$ may be different to each other when q and u are 2, Y represents CO or $NR^5CO$, $R^5$ represents hydrogen, C1–C6 alkyl, optionally-substituted phenyl or optionally-substituted benzyl, with proviso that p is 1 when Y is CO, n is not 0 when p is 1, Y is CO, u is 1, t is 0, m is 1, q is 0, $R^1$ and $R^2$ are hydrogen, and $R^4$ is C1–C6 alkoxy or alkoxycarbonyl, n is not 0 when p is 0 and Y is $NR^5CO$, q is not 2 when p is 0, Y is $NR^5CO$, n is 1 or 2, n is not 2 when Y is $NR^5CO$, p is 1, q is 2, and one of $R^3$ is halogen, q is not 0 and $R^3$ is not alkyl, alkoxy, or halogen when us is 0 and Y is CO, and q is not 0 and $R^3$ is not alkyl or halogen when u is 1 or more, Y is CO and $R^4$ is halogen or alkyl.

2. Phenol compounds represented by a general formula (II);

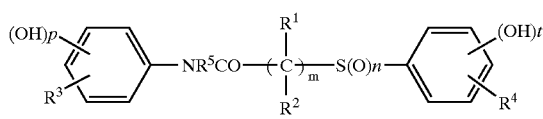

wherein $R^1$ and $R^2$ represent hydrogen or C1–C6 alkyl, m represents an integer of 1 to 6, n represents an integer of 0 to 2, p and t represent an integer of 0 to 3, with proviso that p and t never be 0, concurrently, $R^3$ and $R^4$ represent nitro, carboxyl, halogen, C1–C6 alkyl, C1–C6 alkoxy, C1–C6 alkoxycarbonyl, sulfamoyl, phenylsulfamoyl, C1–C6 alkylsulfamoyl, di(C1–C6 alkylsulfamoyl), carbamoyl, phenylcarbamoyl, C1–C6 alkylcarbamoyl or di(C1–C6 alkylcarbamoyl), and $R^5$ represents hydrogen, C1–C6 alkyl, optionally-substituted phenyl or optionally-substituted benzyl, with proviso that n is not 0 when p is 0.

3. Phenol compounds represented by a general formula (III);

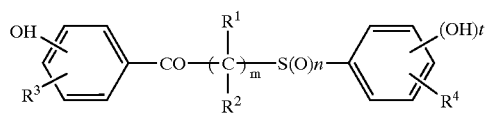

wherein $R^1$ and $R^2$ represent hydrogen or C1–C6 alkyl, m represents an integer of 1 to 6, n represents an integer of 0 to 2, t represents an integer of 1 to 3, $R^3$ and $R^4$ represent nitro, carboxyl, halogen, C1–C6 alkyl, C1–C6 alkoxy, C1–C6 alkoxycarbonyl, sulfamoyl, phenylsulfamoyl, C1–C6 alkylsulfamoyl, di(C1–C6 alkylsulfamoyl), carbamoyl, phenylcarbamoyl, C1–C6 alkylcarbamoyl or di(C1–C6 alkylcarbamoyl), and $R^5$ represents hydrogen, C1–C6 alkyl, optionally-substituted phenyl or optionally-substituted benzyl, and $R^3$ is not alkyl or halogen when $R^4$ is halogen or alkyl.

4. A recording material containing a color forming dye characterized in that the recording material comprises at least one of the phenol compounds represented by a general formula (I)

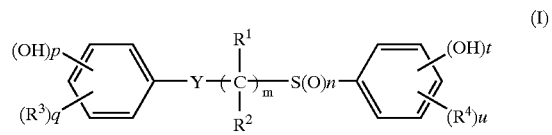

wherein $R^1$ and $R^2$ represent hydrogen or C1–C6 alkyl, m represents an integer of 1 to 6, n represents an integer of 0 to 2, p and t represent an integer of 0 to 3, with proviso that p and t never be 0, concurrently, $R^3$ and $R^4$ represent nitro, carboxyl, halogen, C1–C6 alkyl, C1–C6 alkoxy, C1–C6 alkoxycarbonyl, sulfamoyl, phenylsulfamoyl, C1–C6 alkylsulfamoyl, di(C1–C6 alkylsulfamoyl), carbamoyl, phenylcarbamoyl, C1–C6 alkylcarbamoyl or di(C1–C6 alkylcarbamoyl), q and u represent an integer of 0 to 2, $R^3$ and $R^4$ may be different to each other when q and u are 2, Y represents CO or $NR^5CO$, $R^5$ represents hydrogen, C1–C6 alkyl, optionally-substituted phenyl or optionally-substituted benzyl, with proviso that p is 1 when Y is CO, and n is not 0 when p is 0 and Y is $NR^5CO$.

5. A recording material containing a color forming dye characterized in that the recording material comprises at least one of the phenol compounds represented by a general formula (II);

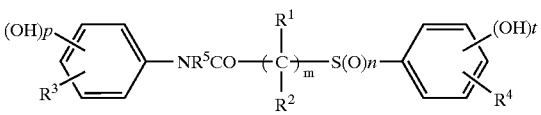

wherein $R^1$ and $R^2$ represent hydrogen or C1–C6 alkyl, m represents an integer of 1 to 6, n represents an integer of 0 to 2, p and t represent an integer of 0 to 3, with proviso that p and t never be 0, concurrently, $R^3$ and $R^4$ represent nitro, carboxyl, halogen, C1–C6 alkyl, C1–C6 alkoxy, C1–C6 alkoxycarbonyl, sulfamoyl, phenylsulfamoyl, C1–C6 alkylsulfamoyl, di(C1–C6 alkylsulfamoyl), carbamoyl, phenylcarbamoyl, C1–C6 alkylcarbamoyl or di(C1–C6 alkylcarbamoyl), and $R^5$ represents hydrogen, C1–C6 alkyl, optionally-substituted phenyl or optionally-substituted benzyl, with proviso that n is not 0 when p is 0.

6. A recording material containing a color forming dye characterized in that the recording material comprises at least one of the phenol compounds represented by a general formula (III);

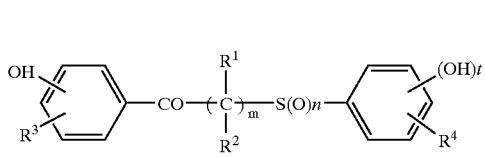

(III)

wherein $R^1$ and $R^2$ represent hydrogen or C1–C6 alkyl, m represents an integer of 1 to 6, n represents an integer of 0 to 2, t represents an integer of 1 to 3, $R^3$ and $R^4$ represent nitro, carboxyl, halogen, C1–C6 alkyl, C1–C6 alkoxy, C1–C6 alkoxycarbonyl, sulfamoyl, phenylsulfamoyl, C1–C6 alkylsulfamoyl, di(C1–C6 alkylsulfamoyl), carbamoyl, phenylcarbamnoyl, C1–C6 alkylcarbamoyl or di(C1–C6 alkylcarbamoyl), and $R^5$ represents hydrogen, C1–C6 alkyl, optionally-substituted phenyl or optionally-substituted benzyl.

7. Phenol compounds represented by a general formula (I);

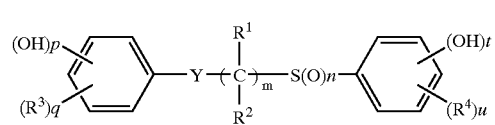

(I)

wherein $R^1$ and $R^2$ represent hydrogen or C1–C6 alkyl, m represents an integer of 1 to 6, n represents an integer of 0 to 2, p and t represent an integer of 0 to 3, with proviso that p and t never be 0 concurrently, $R^3$ and $R^4$ represent nitro, carboxyl, halogen, C1–C6 alkyl, C1–C6 alkoxy, C1–C6 alkoxycarbonyl, sulfamoyl, phenylsulfamoyl, C1–C6 alkylsulfamoyl, di(C1–C6 alkylsulfamoyl), carbamoyl, phenylcarbamoyl, C1–C6 alkylcarbamoyl or di(C1–C6 alkylcarbamoyl), q and u represent an integer of 0 to 2, $R^3$ and $R^4$ may be different to each other when q and u are 2, Y represents CO or $NR^5CO$, $R^5$ represents hydrogen, C1–C6 alkyl, optionally-substituted phenyl or optionally-substituted benzyl, with proviso that p is 1 when Y is CO, n is not 0 when p is 1, Y is CO, u is 1, t is 0, m is 1, q is 0, $R^1$ and $R^2$ are hydrogen, and $R^4$ is C1–C6 alkoxy, n is not 0 when p is 1, Y is CO, u is 0, t is 1, m is 1, q is 0, $R^1$ and $R^2$ are hydrogen, n is not 0 when p is 0 and Y is $NR^5CO$, q is not 2 when p is 0, Y is $NR^5CO$, and n is 1 or 2, and n is not 2 when Y is $NR^5CO$, p is 1, q is 2 or 3, and one of $R^3$ is halogen.

8. Phenol compounds represented by a general formula (I);

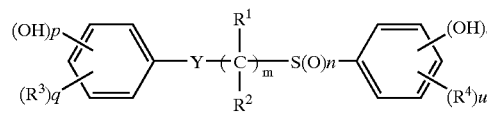

(I)

wherein $R^1$ and $R^2$ represent hydrogen or C1–C6 alkyl, m represents an integer of 1 to 6, n represents an integer of 0 to 2, p and t represent an integer of 0 to 3, with proviso that p and t never be 0 concurrently, $R^3$ and $R^4$ represent nitro, carboxyl, halogen, C1–C6 alkyl, C1–C6 alkoxy, C1–C6 alkoxycarbonyl, sulfamoyl, phenylsulfamoyl, C1–C6 alkylsulfamoyl, di(C1–C6 alkylsulfamoyl), carbamoyl, phenylcarbamoyl, C1–C6 alkylcarbamoyl or di(C1–C6 alkylcarbamoyl), q and u represent an integer of 0 to 2, $R^3$ and $R^4$ may be different to each other when q and u are 2, Y represents CO or $NR^5CO$, $R^5$ represents hydrogen, C1–C6 alkyl, optionally-substituted phenyl or optionally-substituted benzyl, with proviso that p is 1 when Y is CO, n is not 0 when p is 1, Y is CO, u is 1, t is 0, m is 1, q is 0, $R^1$ and $R^2$ are hydrogen, and $R^4$ is C1–C6 alkoxy or alkoxycarbonyl, n is not 0 when Y is CO, n is not 0 when p is 0 and Y is $NR^5CO$, q is not 2 when p is 0, Y is $NR^5CO$, and n is 1 or 2, n is not 2 when Y is $NR^5CO$, p is 1, q is 2 , and one of $R^3$ is halogen, q is not 0 and $R^3$ is not alkyl, alkoxy, or halogen when u is 0 and Y is CO, and q is not 0 and $R^3$ is not alkyl or halogen when u is 1 more, Y is CO and $R^4$ is halogen or alkyl.

9. The phenol compound of claim 1, wherein $R^1$ and $R^2$ each independently represent hydrogen or methyl, m represents an integer of 1 to 4, n represents an integer of 0 to 2, p represents an integer of 1, t represents an integer of 1 or 2, $R^3$ represents methyl, methoxy, chloro or bromo, $R^4$ represents methyl, chloro or bromo, q and u represent an integer of 0 or 1, and Y represents CO.

10. The phenol compound of claim 1, wherein the compound is selected from the group consisting of 2'-hydroxy-2-(4-hydroxyphenylthio) acetophenone, 2'-hydroxy-2-(4-hydroxyphenylsulfinyl) acetophenone, 2'-hydroxy-2-(4-hydroxyphenylsulfonyl) acetophenone, 4'-hydroxy-2-(4-hydroxyphenylthio) acetophenone, 4'-hydroxy-2-(4-hydroxyphenylsulfinyl) acetophenone, 4'-hydroxy-2-(4-hydroxyphenylsulfonyl) acetophenone, and 3'-hydroxy-2-(4hydroxyphenylsulfonyl) acetophenone.

11. The phenol compound of claim 1, wherein wherein $R^1$ and $R^2$ represent hydrogen or methyl, m represents an integer of 1 or 2, n represents an integer of 0to 2, p represents 0 or 1 t represent an integer of 0 to 2, with proviso that p and t never be 0 concurrently, each $R^3$ independently represents methyl, methoxy, chloro, bromo, nitro, methoxycarbonyl, ethoxycarbonyl, carboxyl, methylcarbamoyl, phenylcarbamoyl, dimethylcarbamoyl, sulfamoyl, or phenylsulfamoyl, $R^4$ represents methyl, q represents an integer of 0 to 2, u represents an integer of 0 or 1

Y represents $NR^5CO$, and $R^5$ represents hydrogen, methyl, cyclohexyl, phenyl, or hydroxyphenyl.

12. The phenol compound of claim 1, wherein the compound is selected from the group consisting of 2-(4-hydroxyphenylsulfinyl) acetoanilide, 2-(4-hydroxyphenylsulfonyl) acetoanilide, 2-(4-hydroxyphenylthio)-(2'-hydroxy-5-chloro) acetoanilide, and 2-phenylthio-2'hydroxy-acetoanilide.

13. The recording material of claim 4, wherein $R^1$ and $R^2$ each independently represent hydrogen or methyl, m represents an integer of 1 to 4, n represents an integer of 0 to 2, p represents an integer of 1, t represents an integer of 1 or 2, $R^3$ represents methyl, methoxy, chloro or bromo, $R^4$ represents methyl, chloro or bromo, q and u represent an integer of 0 or 1, and Y represents CO.

14. The phenol compound of claim 1, wherein the compound is selected from the group consisting of 2'-hydroxy-2-(4-hydroxyphenylthio) acetophenone, 2'-hydroxy-2-(4-hydroxyphenylsulfinyl) acetophenone, 2'-hydroxy-2-(4-hydroxyphenylsulfonyl) acetophenone, 4'-hydroxy-2-(4-hydroxyphenylthio) acetophenone, 4'-hydroxy-2-(4-hydroxyphenylsulfinyl) acetophenone, 4'-hydroxy-2-(4-hydroxyphenylsulfonyl) acetophenone, and 3'-hydroxy-2-(4hydroxyphenylsulfonyl) acetophenone.

15. The phenol compound of claim 1, wherein wherein $R^1$ and $R^2$ represent hydrogen or methyl, m represents an integer of 1 or 2, n represents an integer of 0to 2, p represents 0 or 1 t represent an integer of 0 to 2, with proviso that p and t never be 0 concurrently, each $R^3$ independently represents methyl, methoxy, chloro, bromo, nitro, methoxycarbonyl, ethoxycarbonyl, carboxyl, methylcarbamoyl, phenylcarbamoyl, dimethylcarbamoyl, sulfamoyl, or phenylsulfamoyl, $R^4$ represents methyl, q represents an integer of 0 to 2, u represents an integer of 0 or 1

Y represents $NR^5CO$, and $R^5$ represents hydrogen, methyl, cyclohexyl, phenyl, or hydroxyphenyl.

16. The phenol compound of claim 4, wherein the compound is selected from the group consisting of 2-(4-hydroxyphenylsulfinyl) acetoanilide, 2-(4-hydroxyphenylsulfonyl) acetoanilide, 2-(4-hydroxyphenylthio)-(2'-hydroxy-5-chloro) acetoanilide, and 2-phenylthio-2'hydroxy-acetoanilide.

* * * * *